United States Patent [19]

Ries et al.

[11] 4,131,026
[45] Dec. 26, 1978

[54] ULTRASONIC TESTING OF SEAMS

[75] Inventors: Karl Ries; Dieter Kaiser, both of Mülheim; Klaus-Uwe Jannsen, Lintorf, all of Fed. Rep. of Germany

[73] Assignee: Mannesmannrohren-Werke AG, Dusseldorf, Fed. Rep. of Germany

[21] Appl. No.: 641,910

[22] Filed: Dec. 18, 1975

[30] Foreign Application Priority Data

Dec. 19, 1974 [DE] Fed. Rep. of Germany ....... 2460713

[51] Int. Cl.² ............................................ G01N 29/04
[52] U.S. Cl. ......................................... 73/625; 73/638
[58] Field of Search .............. 73/67.5 R, 67.7, 67.8 R, 73/67.8 S, 67.9, 71.5 US, 625, 638, 640, 641

[56] References Cited

U.S. PATENT DOCUMENTS

| 2,846,875 | 8/1958 | Grabendorfer | 73/67.8 R |
| 3,213,676 | 10/1965 | Makous | 73/625 |
| 3,323,354 | 6/1967 | Daubresse | 73/67.8 S |
| 3,512,399 | 5/1970 | Weinbaum | 73/67.8 R |
| 3,552,191 | 1/1971 | Heseding | 73/67.7 |
| 3,575,044 | 4/1971 | Gibbs et al. | 73/625 |
| 3,608,361 | 9/1971 | Krautkramer et al. | 73/67.7 |
| 3,850,027 | 11/1974 | Nakanishi et al. | 73/625 |
| 3,868,847 | 3/1975 | Gunkel | 73/625 |

Primary Examiner—Stephen A. Kreitman
Attorney, Agent, or Firm—Smyth, Pavitt, Siegemund, Jones & Martella

[57] ABSTRACT

The seam of a pipe is tested sequentially from various directions and with differently directed test beams to search for differently oriented defects, and repeatedly for stepwise testing each portion of the same.

7 Claims, 6 Drawing Figures

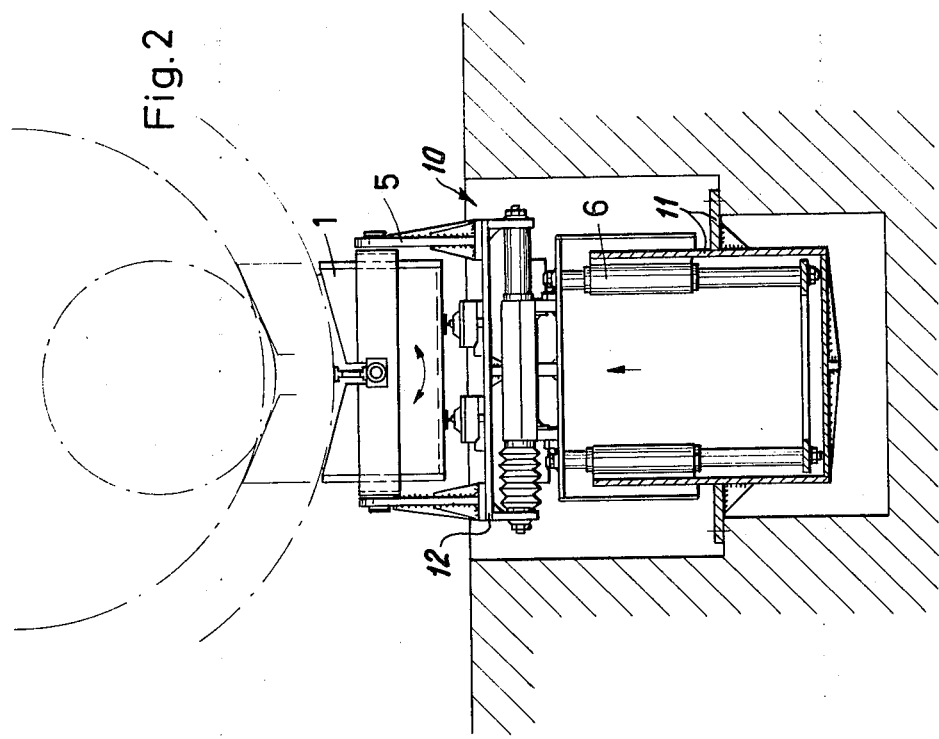
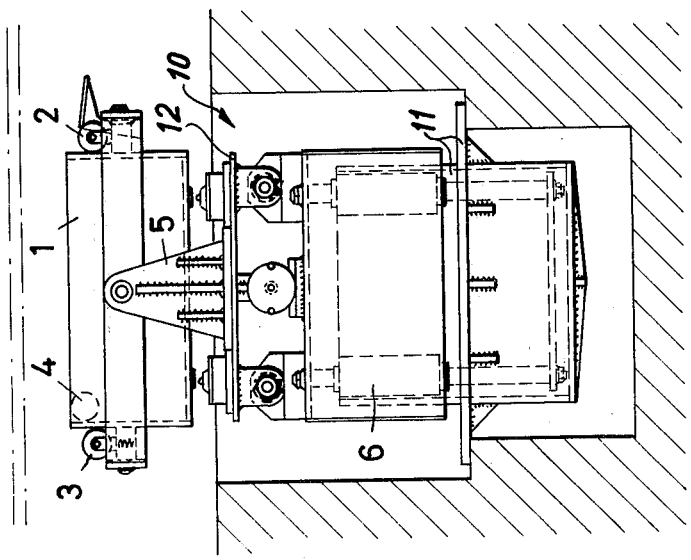

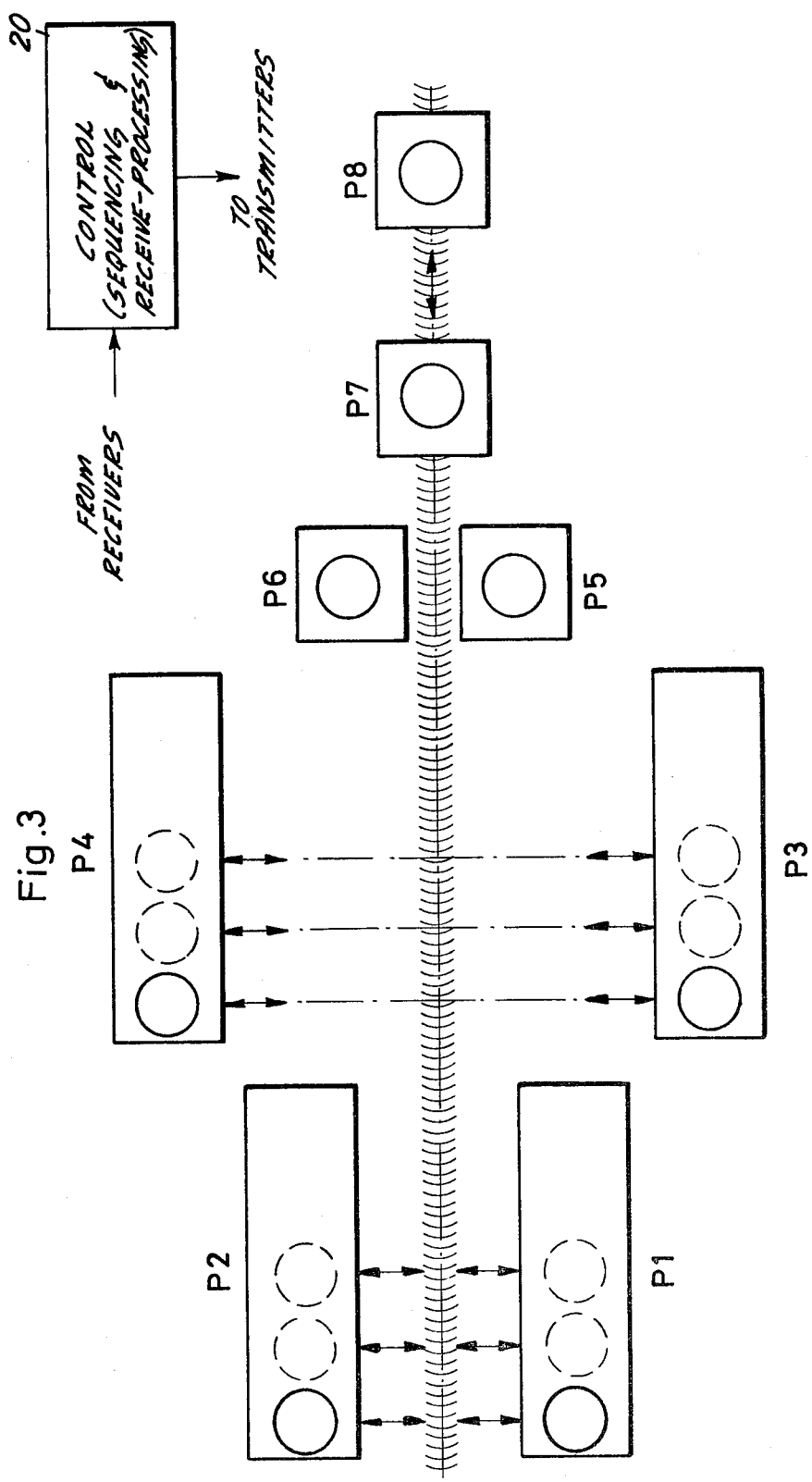

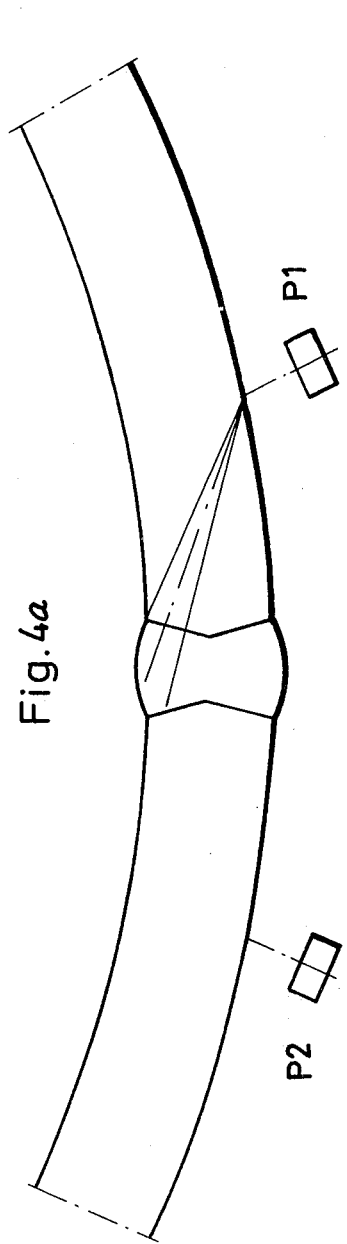
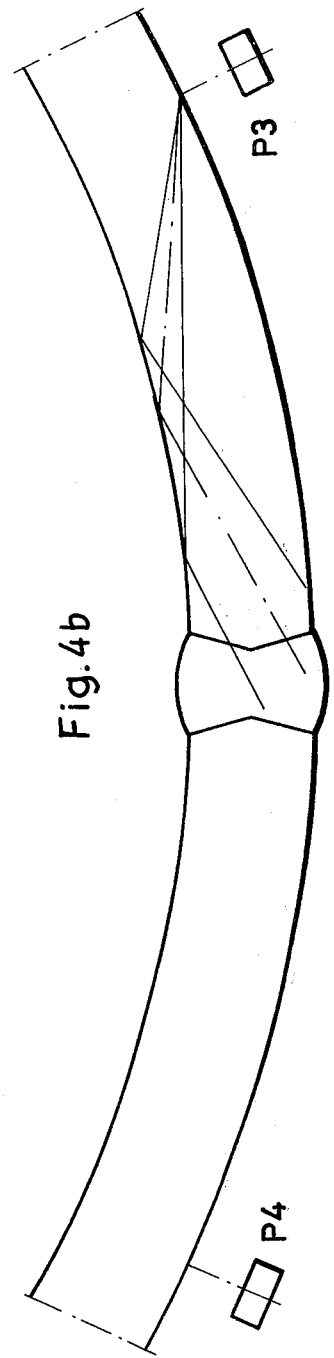

4,131,026

ULTRASONIC TESTING OF SEAMS

BACKGROUND OF THE INVENTION

The present invention relates to ultrasonic testing of a welding seam and of border zones thereof, particularly of submerged arc-welded pipes.

It is known to test seamless pipes by means of ultrasonic radiation, whereby the pipe is dipped into or at least in contact with a liquid serving as a transmission and coupling medium for ultrasonic waves. Having found a deviation from normal, the pipe is subsequently examined, e.g., by means of X-rays, because the known methods of ultrasonic testing do not yield sufficient accurate data.

DESCRIPTION OF THE INVENTION

It is an object of the present invention to provide a method and equipment for testing the welding seam of pipes as to defects, using particularly ultrasonics and preferably with such a degree as to localization and detail, so that X-raying of the seam is no longer needed.

In accordance with the preferred embodiment of the present invention, it is suggested to stepwise test portions of the welding seam by means of ultrasonics and sequentially as to each portion and on a highly localized basis, (but not necessarily in the following sequence), for locating longitudinally extending defects in the seam, transversely extending defects in the seam, and edge zone defects. At least, the pipe seam and adjacent material as well as the test heads are submerged in coupler fluid.

Testing involves in each instance directing ultrasonic energy towards the seam (but from different directions as to the different types of tests) for probing a well-defined portion of the seam and detecting the interaction of the energy with that portion of the seam resulting in signals received by appropriately positioned receivers. These signals are processed as to transmit time and/or contour. On the basis of the known spacing between the several ultrasonic transmitters and receivers and under consideration of the speed of the pipe tested as it moves past the equipment and under further consideration of the sequencing of testing (transmission of ultrasonic energy), the test results for the same or closely adjacent zones of and in the seam can readily be correlated, even though the specific tests have been conducted at different times, to obtain a rather detailed representation of any defects, its location, extension, contour, etc. Particularly, the correlation of the several tests as to the same seam portion permits classification of the defects. The correlation of transmit time representation and signal contour yields significant results.

The emission of ultrasonic pulses (bursts) and observation of the reflection thereof by different interfaces of the seam and/or the pipe is preferred, whereby preferably the test equipment is disposed on the outside and below the pipe. One may, however, use, at least in parts straight-through transmission. Upon using reflection, the test for longitudinally extending defects is preferably divided into two parts in that zones of the welding seam closer to the inner bead boundary and zones closer to the outer bead boundary are separately tested by causing reflections of a test beam respectively at the inner and outer boundary, which in the latter case requires employment of internal reflection of the beam on the inside surface of the pipe; the transmitters are spaced from the seam accordingly.

Use of monitor aperture stops permits distinction between errors in the pipe material and in the seam, while double reflection permits association of the particular test with a particular depth zone of and in the seam. It was found that upon practicing the method of the invention, the detection of defects is sufficiently detailed and localized, so that subsequent X-raying is no longer needed.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a side view, partially in section of equipment for practicing the preferred embodiment of the invention;

FIG. 2 is a front view, also partially in section of the same equipment shown in FIG. 1;

FIG. 3 is an elevational view of test heads used in the equipment of FIGS. 1 and 2;

FIGS. 4a and 4b show particularly arranged test heads of FIG. 3 in side view; and FIG. 5 is a block diagram for a processing circuit.

Proceeding now to the detailed description of the drawings, the FIGURES show a pit 10 in a suitable foundation and in which is mounted a frame 11 for an elevator platform 12 constructed as a carriage and being held by a lifting device 6. The lifting device is comprised, e.g., of hydraulic cylinders for raising and lowering platform 12, and the latter in turn can move laterally in a direction that extends transversely to the axis of the pipe to be tested (transverse to the plane of the drawing of FIG. 1). Raising and lowering of the platform is needed to adapt the test equipment to the height of the pipe as it passes along the test equipment. The various dash-dot circles in FIG. 2 and the phantom outlining of a structure show in addition here the different possibilities of positioning the equipment in relation to a pipe to be tested.

The carriage 12 has a cardan mounting frame 5 for suspending a container 1. The container 1 is filled with accoustic coupler fluid of a type known for that purpose and has support and guide rolls 4 for a pipe, which is being moved along the test equipment. Moreover, the container 1 has in the front a rigid guiding device, such as a grooved pulley or the like to scan along the welding seam to be tested, while a second similar guiding device 3 is resiliently mounted to the rear of the container. "Front" and "rear" in this context is related to the direction of movement of a pipe past the equipment. The grooved guide wheels engage the bulging seam and cause the cardanically suspended container to maintain its orientation to the passing pipe.

A plurality of test heads P 1 through P 8 is mounted in the container and at an orientation to the pipe to be tested as shown in FIG. 3 and 4a, 4b. Particularly, one can see that several of the test heads are disposed alongside of but laterally displaced from the passing welding seams. Others are directly in line and underneath the welding seam.

The two test heads P 1 and P 2 form a first pair and are arranged as shown in FIGS. 3 and 4a. Each of the heads of this pair has at least three, but preferably even more, e.g., six individual ultrasonic oscillating transducers (transmitters). These transmitters may be mounted in the respective head at differently adjusted angles. Each head includes at least one receiver but may include a corresponding number of receivers.

The two test heads P 1 and P 2 are arranged so that ultrasonic radiation reflects on the inside portion of the welding seam, i.e., on the interface of the bead with the interior of the pipe to be tested. If the test head P 1 operates as transmitter then the symmetrically disposed receiver in head P 2 will receive a certain amount of reflected ultrasonic energy, and the receiver in head P 1 receivers echo signals including an echo from any longitudinally extending defect. Additionally, such a defect will weaken the signal received by head P 2 so that the contour of that signal is distorted if compared with signals from defectless seam portions. Conversely, an ultransonic beam radiated from head P 2 is reflected towards head P 1 while an echo is received also in head P 2. In particular, it can be seen that the test beam as effective has penetrated primarily the zone of the welding seam close to the reflecting boundary. These test heads, therefore, will detect longitudinal defects in the welding seam being located closer to the inside thereof. Probing the seam from opposite sides is desirable because contour and orientation of a defect may not produce a sufficient echo in one direction.

The two heads P 3 and P 4 are disposed a little farther from the welding seam, so that radiation of one head (e.g., P 3) and after having propagated into the pipe's wall is reflected first on the inside of the pipe, i.e., on the interface of the pipe with the interior thereof. Thus, the reflected beam or beam portion now is directed with a radial outward component towards the welding seam and here particularly towards that portion of the welding seam which is rather close to the outer beam-bead boundary. Thus, these test heads will detect longitudinal defects more in the outer zone of the welding seam. Further reflection occurs in symmetric fashion and will cause a portion of the ultrasonic radiation to reach the respective other symmetrically disposed head which in the example of FIG. 4b is the head P 4. An echo will return along the incident path to head P 3. Transmission by head P 4 reverses the situation to probe the seam from the other side.

Each of the test heads has, for example, six vibration transducers or transmitters, and preferably these transmitters have a slightly different orientation with regard to the center axis of emitting ultrasonic waves. Therefore, the maximum intensity and center portion of each beam can be made to impinge upon and traverse different zones of the welding seam, so that a very detailed (high resolution) study and test is obtained. In the FIGS. 4a and 4b the emission is presumed to occur from the respective transducers in a particular direction towards the pipe so that a particular test beam results from reflection inside of the pipes. Upon shifting the center axis of the respective transmitter to a slightly different angle, a slightly differently oriented test beam will reach the welding seam, particularly as far as its intensity distribution about the center axis of the beam is concerned.

The test heads P 5 and P 6 are disposed very close to the edges of the seam, and they are provided, therefore, for individually testing the edge and border zones of the welding seam. Each of these heads has two vibrators, one operating as transmitter, the other as receiver in each instance. Thus, they operate in accordance with the transmitter/receiver mode. The test beam traverses an edge zone, is reflected and traverses again the same or the other edge zone. The other heads $P_1$ to $P_4$ and $P_7$, $P_8$ each have just one vibrator and operate either in the transmit or in the receive mode and in pairs as described.

The pair of test heads $P_7$ and $P_8$ are disposed in longitudinally spaced apart relation and directly underneath the welding seam to test the presence of transversely extending defects. By operating both heads alternatingly in the transmitter mode, but concurrently in the receiving mode, one can more readily localize any defect as each defect will be traversed by an ultrasonic beam from one side and subsequently from the other side. The test beam is basically reflected back towards the receiver in the respective other head by the inner boundaries of the interface of the welding seam in the interior of the pipe, and an echo resulting from reflection by a defect reaches the same head whose transmitter transmitted the test beam. These operations are analogous to FIG. 4a except that the plane of reflection extends transversely to the plane of the drawings of the FIGURE.

The test heads are all connected to a control circuit or unit 20 which may be disposed in some suitable place on the carriage 12 or even remote from the equipment and connected with the test heads in container 1 (FIGS. 1 and 2) through suitable flexible cable. The control unit 20 includes a sequencer to run the transmitters in cyclically repeated sequence. The system 20 includes, additionally, a processing circuit. The receiver output lines of the test heads feed one or several amplifiers. Since the circuit 20 produces sequencer signals for control and enabling of the test heads, the signals identify the respective test head and transmitter and receiver so that, for example, a computer can correlate the output signals of the amplifiers with specific portions of the seam. Additionally, the leading edge of any control signal for control of a ultrasonic signal burst demarks a zero point in time from which one can determine the transit of transmission time of the respective ultrasonic bursts. This is particularly relevant, of course, for echo detection.

Further details of circuit 20 do not have to be discussed. Suffice it to say that the circuit has available the time of arrival of each receiving signal, the wave shape and contour thereof, the time of transmission and the time of an echo as well as identification of the respective test area. These signals can be used in any desired way, for example, stored, plotted and processed as analog and/or digital signals. One type of processing, however, should be mentioned specifically; the beginning of each burst of transmission is demarked by the leading edge of a control signal. The receipt of a transmitted ultrasonic signal as such can be detected per se and used as timing signal to be related in time to the time of transmission for metering the transit time. Moreover, relevant signals will arrive only within particular short periods, so that unwanted, parasitic echos, etc. should be suppressed.

The propagation time of the pipe as a whole past the test equipment is sufficiently slow, so that the testing can be carried out with sufficient detailing. Each individual test involves only a limited seam portion; one can say that the seam is being hypothetically segmented into mm segments and each segment is separately tested as to longitudinal, transverse and edge zone defects. The spacing of the several transducers along the seam may be selected to have an integral numerical relation to the test sequency, so that, for example, by counting additionally the number of sequencer cycles and by identifying each test result therewith, one may correlate later, for example, digitally all the test results for any particular welding zone or segment.

It should be mentioned finally that the test method is applicable to the testing of the quality of the welding seam of any kind of pipe but testing of submerged are welded pipes, particularly large pipes, is particularly critical. The test results as acquired may then be processed further, for example, in a computer, which assembles a complete representation of the state of the welding seam along the entire length of the pipe. It was found that employment of the pulse echo method is of particular advantage. However, in cases the transmit-receiving mode of operation can be used to a larger extent than has been outlined above with reference to the heads P 5 and P 6. In any event, it was found that the test result is sufficiently detailed so that subsequent X-raying is no longer needed.

The invention is not limited to the embodiments described above but all changes and modifications thereof not constituting departures from the spirit and scope of the invention are intended to be included.

We claim:

1. Method of testing the welding seam of pipes, comprising:
   providing coupler fluid for contacting the pipe through which ultrasonic energy can be applied to and received from the pipe;
   (i) directing plural beams of ultrasonic energy from lateral directions without longitudinal component towards the welding seam, each beam being at right angles in relation to the longitudinal extension of the seam entering the pipe at different but fixed lateral distances from the seam, and detecting the interaction of the beams energy with different portions of the seam to obtain signal representations of the interactions including representation of any longitudinal defect in the said portion of seams, the energy being coupled to and from the pipe outside of the seam proper;
   (ii) directing ultrasonic energy towards the edges of the seam detecting interaction of the energy with a portion of the edges to obtain signal representation of such interaction including representation of any defect in such portions;
   (iii) directing ultrasonic energy towards the seam from a longitudinal direction without transverse component and independently from step (1) and detecting from another longitudinal direction the interaction of the energy with a portion of the seam to obtain a signal representation of the interaction including representation of any transversely extending defect in the latter portion of the seam;
   repeating the steps (i), (ii), (iii) sequentially on progressing portions of the seam in longitudinal direction to sequentially test the entire seam; and
   processing the said signal representation as obtained pursuant to the steps (i), (ii), (iii) as repeated to obtain representation of the respective signal contour and of the transition times in each instance for identifying defects on the basis of correlated responses of sequential steps (i) and (iii).

2. Method as in claim 1, wherein said plurality of steps includes step (*a*) for directing ultrasonic energy from outside of the pipe towards the inner boundary of the seam and a step (*b*) for directing ultrasonic energy for reflection at the inner wall of the pipe towards the outer boundary of the seam.

3. Method as in claim 1 wherein the step (iii) is carried out by passing the pipe past transmitting and receiving transducers in radial alignment of the transducers with the seam.

4. Method as in claim 1 wherein the step (ii) is carried out by passing the pipe past transmitting and receiving transducers each being approximately radially aligned with one of the edges of the seam.

5. Method as in claim 1, wherein said step (i) is carried out alternately as to transmission of ultrasonic energy from the lateral and the other, also lateral direction, and the receiving alternates inversely accordingly.

6. Method as in claim 1, wherein said step (iii) is carried out alternately from the longitudinal direction and from the other longitudinal direction, the detection alternates inversely accordingly.

7. Method as in claim 1, wherein the steps (i) and (iii) are carried out by means of transducers having a single oscillating element that alternates in a transmitting and in a receiving mode.

* * * * *